United States Patent
Koster, Jr.

(10) Patent No.: US 6,689,147 B1
(45) Date of Patent: *Feb. 10, 2004

(54) ANASTOMOSIS PUNCH DEVICE AND METHOD

(76) Inventor: J. Kenneth Koster, Jr., 3520 Point Pleasant Rd., Jacksonville, FL (US) 32217

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 223 days.

(21) Appl. No.: 09/593,976

(22) Filed: Jun. 13, 2000

(51) Int. Cl.[7] ............... A61B 17/32; A61B 17/34; A61B 17/08; A61D 1/00
(52) U.S. Cl. ............... 606/184; 606/185; 606/151; 606/213
(58) Field of Search ............... 606/184, 185, 606/159, 167, 567, 213, 215, 232, 153, 170, 180; 604/22, 32; 128/898; 600/567

(56) References Cited

U.S. PATENT DOCUMENTS

| 5,292,310 | A | * | 3/1994 | Yoon | 600/566 |
|---|---|---|---|---|---|
| 5,342,382 | A | * | 8/1994 | Brinkerhoff et al. | 604/164.11 |
| 5,779,724 | A | * | 7/1998 | Werner | 30/162 |
| 5,817,113 | A | * | 10/1998 | Gifford et al. | 606/151 |
| 5,827,316 | A | * | 10/1998 | Young et al. | 606/185 |
| 5,910,153 | A | * | 6/1999 | Mayenberger | 606/184 |
| 5,944,730 | A | * | 8/1999 | Nobles et al. | 606/151 |
| 6,022,367 | A | * | 2/2000 | Sherts | 606/184 |
| 6,080,173 | A | * | 6/2000 | Williamson et al. | 600/567 |
| 6,235,045 | B1 | * | 5/2001 | Barbut et al. | 128/898 |
| 6,344,026 | B1 | * | 2/2002 | Burbank et al. | 600/567 |

* cited by examiner

Primary Examiner—Michael J. Milano
Assistant Examiner—Paul A Roberts
(74) Attorney, Agent, or Firm—Thomas C. Saitta

(57) ABSTRACT

An anastomosis punch device, and method of using same, for creating a circular hole in the aortic wall, where the device also segregates the hole from the blood flow path such that no blood is lost through the hole during attachment of the vein graft. The invention is a hand-held punch comprising an elongated housing to be gripped by the surgeon, the housing retaining in a coaxially aligned manner a distally extended punch head and cutting disk mounted onto a shaft, a cutting sleeve having a distal cutting rim which cuts a circular plug in cooperation with the punch head, an umbrella-like flexible dam formed of an elastic material and adjoined to the punch shaft adjacent said punch head in a manner which allows it to be deployed radially outward with the enlarged open rim facing the proximal direction, and a deployment ram movable axially relative to the dam to spread open the dam.

8 Claims, 5 Drawing Sheets

ANASTOMOSIS PUNCH DEVICE AND METHOD

BACKGROUND OF THE INVENTION

This invention is a medical device and relates generally to the field of punch devices used in performing anastomosis (the joining of a hollow or tubular organ to another hollow or tubular organ), and in particular such devices used in the surgical joining of a vein graft to the aortic wall, where the punch device is used to create the hole in the aortic wall.

In coronary bypass surgery, a blocked segment of the coronary artery is bypassed by attaching a vein graft to the aorta above the blocked point and to the artery downstream of the blocked point, such that blood flow is routed around the blockage through the vein graft. In a common technique used to attach the graft, a hole is created in the aortic wall by first creating a small slit using a scalpel. The cutting disk of a punch device is then inserted through the slit. The cutting disk is mounted onto a thin shaft, which is coaxially received by a tubular sleeve member, the end of which is provided with an annular cutting edge or rim. With the aortic wall between the disk and the sleeve, either the disk is retracted into the sleeve or the sleeve is advanced beyond the disk. This operation cuts a circular opening in the aortic wall, and the plug cut from the wall is entrapped within the, sleeve and disk. The punch device is then removed and the surgeon proceeds with the anastomotic procedure.

It is necessary to temporarily occlude the opening in the aortic wall in some manner after removal of the plug to prevent excessive loss of blood during the anastomotic procedure. The most commonly employed method is to apply a C-shaped surgical clamp to the side of the aortic wall at the proposed site of the anastomosis prior to cutting the aorta and introducing the punch. The clamp compresses only a portion of the aorta, allowing continued blood flow past the clamped area. This technique can be problematic in that application of the clamp may cause damage to the aorta or release plaque fragments or atheromatous debris into the blood stream when the clamp is released.

One alternative technique for blocking blood flow through the hole created in the aortic wall by a combination punch device is shown in U.S. Pat. No. 5,944,730 of Nobles et al. The Nobles et al. device, as described in the second embodiment of the disclosure, is a grossly elongated instrument having an occluding inverting member mounted onto the distal end of a long, slender flexible tube, an inverter handle assembly, and an intermediately disposed punch assembly. The punch assembly is joined to the inverter handle assembly in a disconnectable fashion, such that the punch assembly is detached from the inverter handle assembly and slid distally along the flexible tube to remove the plug from the aortic wall, after which it is translated proximally and rejoined to the inverter handle assembly. The inverter handle assembly is then manipulated to cause the inverting member to fold onto itself into a conical configuration and the entire device is pulled in the proximal direction to seal the aortic wall. Each end of the inverting member must be attached to a different elongated tubular member which are slidably movable in the axial direction relative to each other. The provision of separable punch and inverter handle assemblies, the elongated flexible tube on which is mounted the occluding member, and the overly complicated design of the occluding member results in an awkward instrument of excessive length which is difficult to operate in an efficient and straightforward manner. Additionally, there is no structure to block blood flow through the hole in the aortic wall during the time period while the punch assembly is being withdrawn and rejoined to the inverter handle assembly prior to expansion of the inverting member and retraction of the apparatus.

It is an object of this invention to provide an anastomosis punch device for creating a hole in the aortic wall, and method of use for same, which has an occluding structure to prevent blood from exiting the hole created in the aortic wall during attachment of the vein graft, where the device comprises an elastic dam membrane having circumferentially spaced longitudinal ribs, where the ribs may be spread to open the membrane into a conical configuration in an umbrella-like manner to surround the hole, then collapsed for withdrawal after the vein has been partially secured, where the dam is affixed to the shaft of the punch assembly distal to the annular cutting disk and the cutting sleeve, where the cutting sleeve blocks blood flow through the hole created in the aortic hole prior to expansion of the elastic dam membrane, such that the punch device is a compact instrument which is easily manipulated by the surgeon.

SUMMARY OF THE INVENTION

The invention comprises an anastomosis punch device, and method of using same, for creating a circular hole in the aortic wall, where the device also segregates the hole from the blood flow path such that no blood is lost through the hole during attachment of the vein graft. The invention is a compact hand-held punch comprising an elongated housing to be gripped by the surgeon, the housing retaining in a coaxially aligned manner a cutting disk, a cutting sleeve having a distal cutting rim which cuts a circular plug in cooperation with the cutting disk, an expandable, umbrella-like, flexible dam formed of an elastic tubular material and adjoined to the shaft of the punch assembly distally to the cutting disk and cutting sleeve in a manner which allows it to be deployed radially outward with the enlarged open rim facing the proximal direction, and a deployment ram movable axially relative to the dam to spread open the dam. The surgeon inserts the punch head, the elastic dam and cutting disk through the aortic wall, then advances the cutting sleeve against and over the cutting disk to remove a circular plug of aortic wall, with the plug being retained within a chamber defined by the cutting sleeve and the cutting disk and the cutting sleeve locked in the advanced position. The ram is then advanced relative to the dam, causing the proximal end of the dam to spread outwardly to form a cone shape, and the ram is locked in position. The rim of the expanded dam is then drawn against the interior wall of the aorta, thus forming a conical dam about the hole. The vein graft is then attached to the aortic wall at the hole using known suturing techniques while the device remains in place. Once the vein is sufficiently attached to the aortic wall in loose manner, the ram is retracted relative to the dam, allowing the dam to collapse into the passive configuration with minimal diameter because of the elastic nature of the membrane. The entire device is then withdrawn between the sutures and completely out of the aorta, with the sutures then quickly tightened to connect the vein graft to the aorta.

DETAILED DESCRIPTION OF THE INVENTION

With reference to the drawings, the invention will now be described in detail with regard for the best mode and the preferred embodiment.

Figure 1:
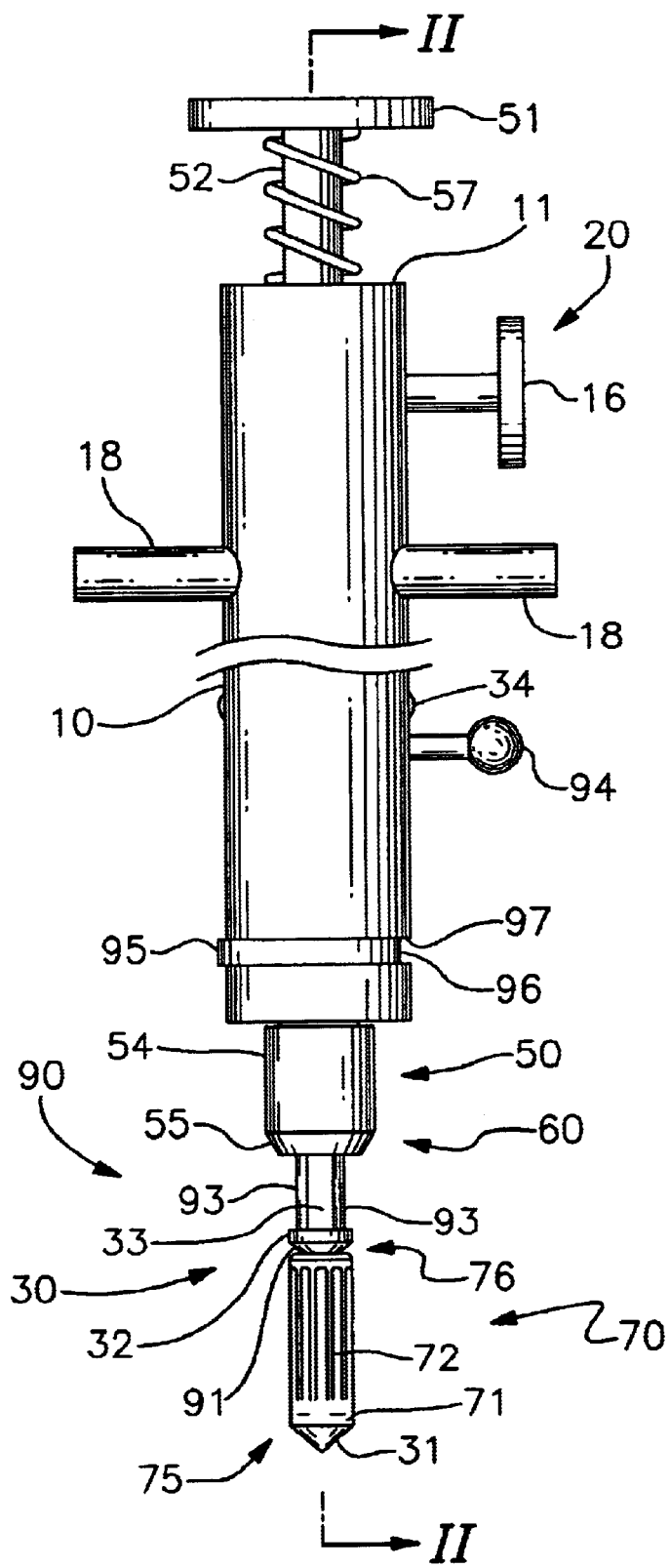
FIG. 1 is an external side view of the device.
Figure 2:
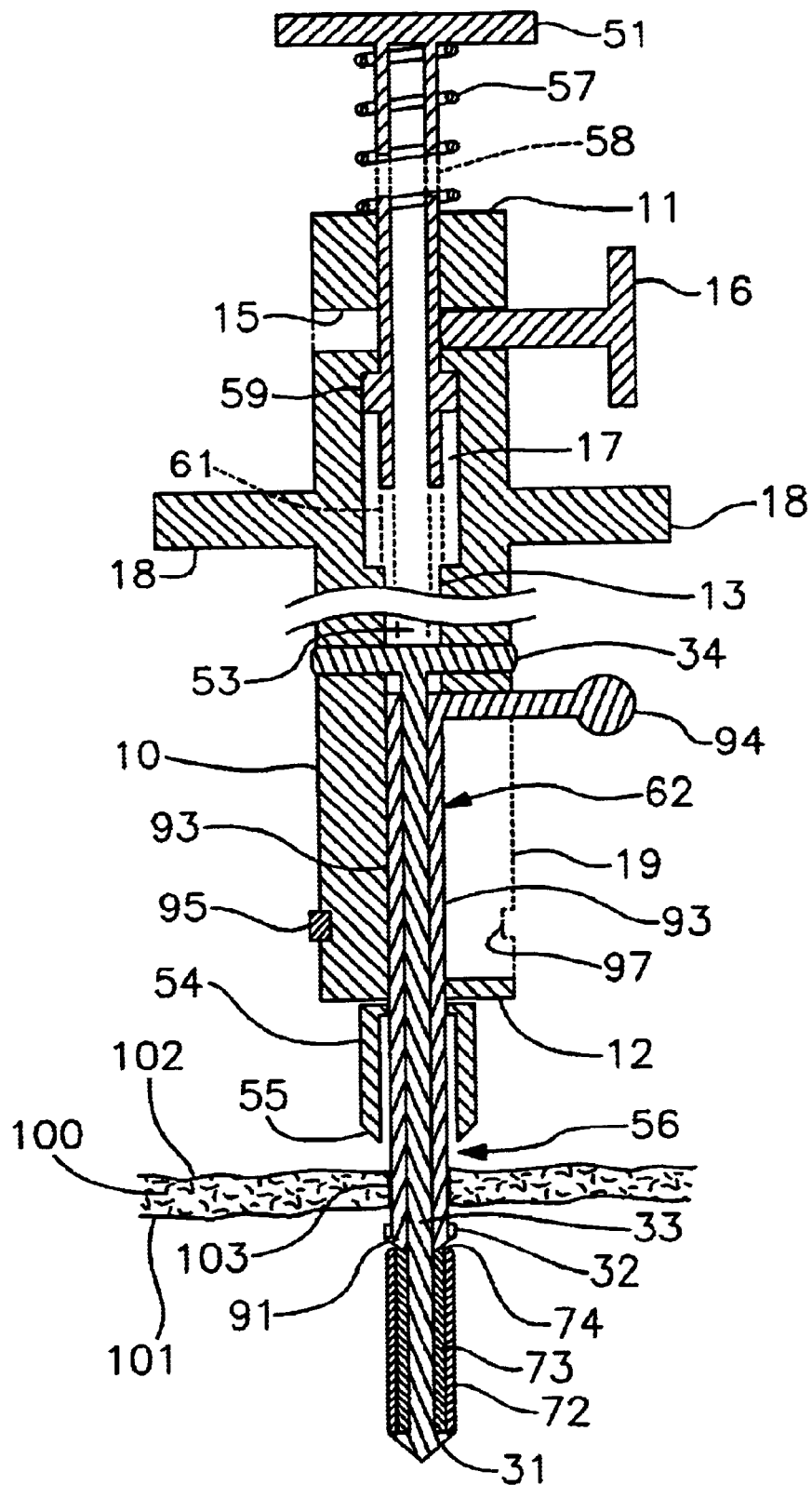
FIG. 2 is a cross-sectional view showing the punch head, elastic dam assembly and cutting disk of the device as inserted into the aortic wall, taken along line 11—11 of FIG. 1.
Figure 3:
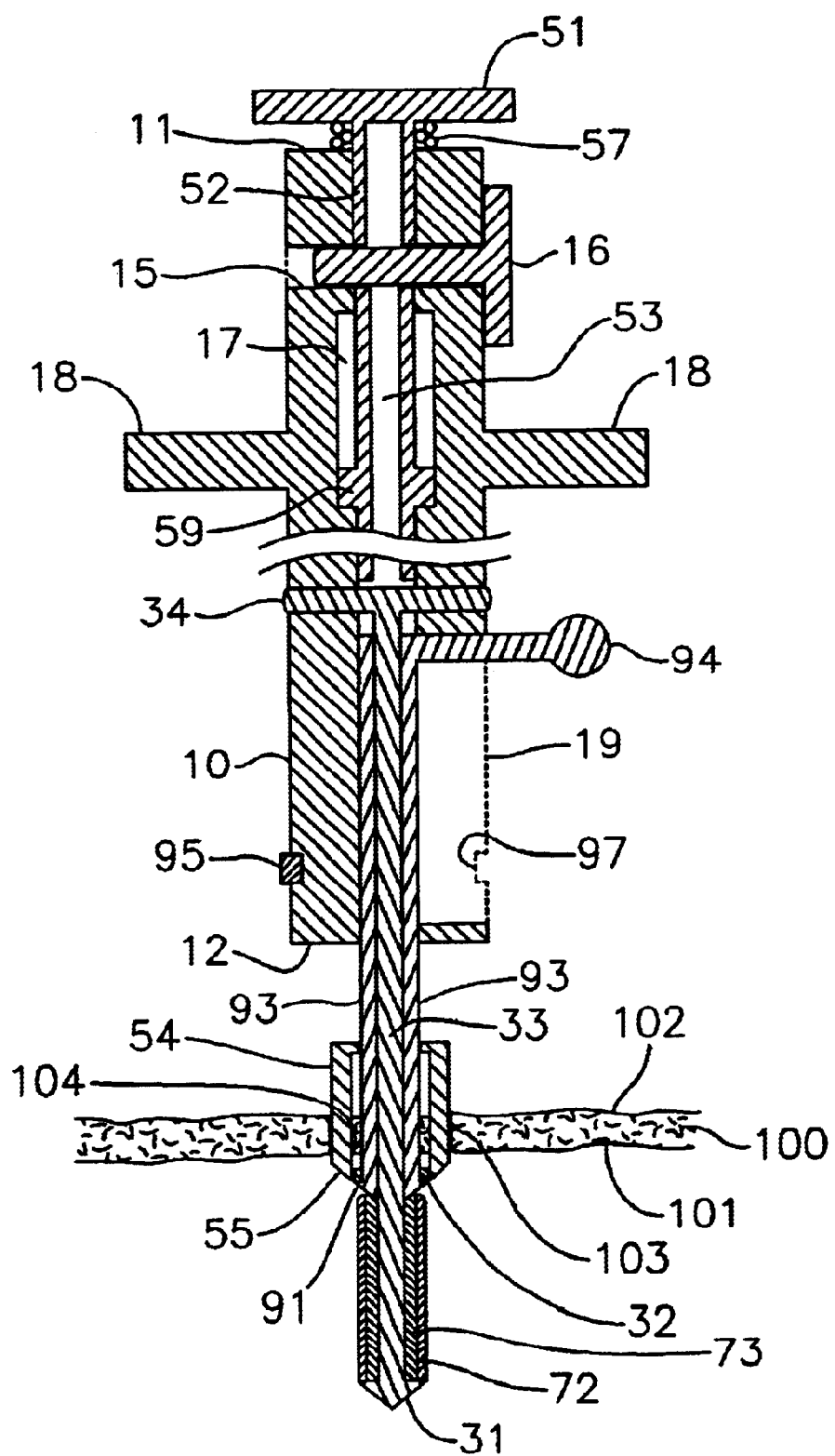
FIG. 3 is a cross-sectional view similar to FIG. 2, showing the plug removed from the aortic wall.

As shown generally in FIG. 1, the invention is an anastomosis punch device comprising a generally elongated, tubular instrument housing 10, a punch assembly 30, a cutting sleeve assembly 50, an elastic dam assembly 70 and a deployment ram assembly 90. The device is configured as an integral apparatus of compact design so as to be easily gripped and manipulated by surgeon. For example, a device having a housing 10 approximately 9 cm in length and approximately 8 mm in diameter, with the distal portion of the punch assembly 30 extending only about 4 cm from the distal end 12 of the housing 10, is representative of a very suitable size. With reference also to FIG. 2, the elongated instrument housing 10 is shown to comprise a proximal end 11 and a distal end 12, where the distal end 12 is the end positioned against the aortic wall 100 during use. For purposes of this disclosure, references to the distal direction or a distal element shall mean the direction or element toward the aortic wall 100 with the device in use, while references to the proximal direction shall means the opposite direction, i.e., external to away from the aortic wall 100. A pair of laterally extending finger grips 18 are externally mounted on the instrument housing 10, preferably approximately 4 cm from the proximal end 11 of the instrument housing 10. A first coaxial cylindrical bore 13 extends from the proximal end 11 within the body of instrument housing 10 to the distal end 12. Cutting sleeve locking means 20, comprising as shown a transverse bore 15 extending into the first bore 13, is provided near the proximal end 11 to receive a sleeve locking pin 16, which is used to secure the cutting sleeve assembly 50 in the advanced position relative to the instrument housing 10, as shown in FIG. 3. Equivalent constructions for cutting sleeve locking means 20 may be utilized as well. A longitudinally extending sleeve guide slot or pair of slots 17 is provided in first bore 13, the sleeve guide slot 17 receiving the guide tabs 59 mounted onto the tubular shaft 52 of the cutting sleeve assembly 50 to prevent rotation of the cutting sleeve assembly 50 within the instrument housing 10 to maintain proper alignment between the transverse bore 15 and a pin receiving aperture 58 located in the tubular shaft 52. A longitudinally extending ram guide slot 19 is provided adjacent to or toward the distal end 12 of the instrument housing 10 to provide a channel for controlled movement of the handle 94 of the deployment ram assembly 90 in either axial direction.

Means 60 to create a circular opening 103 in the aortic wall 100 comprise in combination punch assembly 30 and cutting sleeve assembly 50. Punch assembly 30 is mounted coaxially within instrument housing 10 with a portion extending from the distal end 12 of the instrument housing 10. Punch assembly 30 comprises a punch head 31 mounted onto a shaft 33, with the shaft 33 fixed within the instrument housing 10 by detent member 34. The punch head 31 is a conical or bladed member with a sharp cutting edge or point such that relatively easy penetration can be attained through the aortic wall 100 by direct pressure on the exterior side 102 of the aortic wall 100. An annular rim or disk member 32, preferably about 3 to 6 mm in diameter, is positioned intermediately on shaft 33 with the edge of the disk 32 having a relatively sharp lip.

The outer diameter of the disk 32 is sized to correspond to the internal diameter of the annular cutting rim 55 and cutting sleeve 54 of the cutting sleeve assembly 50, the outer diameter of disk 32 being only slightly smaller than the internal diameter of cutting rim 55 and cutting sleeve 54, such that the cutting rim 55 and cutting sleeve 54 can be advanced over the disk 32 to produce a cutting action to remove a circular plug 104 from the aortic wall 100, as shown in FIG. 3.

Cutting sleeve assembly 50 is coaxially positioned within instrument housing 10, fitting within first bore 13 such hat sliding movement of the cutting sleeve assembly 50 relative to the instrument housing 10 and punch assembly 30 in the axial direction is possible. Cutting sleeve assembly 50 comprises a tubular shaft 52 which extends from both the distal end 12 and the proximal end 11 of the instrument housing 10. A flange handle or button 51 is mounted onto the proximal end of the tubular shaft 52, allowing the cutting sleeve assembly 50 to be advanced by pressure from the surgeon's thumb or palm A spring member 57 is mounted between the proximal end 11 of the instrument housing 10 and the button 51, and biases the cutting sleeve assembly 50 in the retracted proximal direction until sufficient pressure is applied to advance it in the distal direction. The tubular shaft 52 defines a coaxial bore 53 which snugly receives the shaft 33 of the punch assembly 30. A pin receiving aperture 58 is positioned toward the proximal end of the tubular shaft 52, sized to receive sleeve locking pin 16 when the sleeve cutting assembly 50 is advanced, as shown in FIG. 3. One or more longitudinally extending guide tabs 59 are provided on the exterior of tubular shaft 52, the guide tabs 59 being received by sleeve guide slots 17 to preclude relative rotation of the cutting sleeve assembly 50 and tho instrument housing 10. Longitudinal slots 61 are provided on the tubular shaft 52 to allow axial movement of the tubular shaft 52 past the punch detent member 34. A ram opening 62 extends along the distal portion of the tubular shaft 52 contained within the housing 10 and through a portion of the cutting sleeve 54 to allow passage of the parallel shafts 93 on the run assembly 90.

The distal end of the cutting sleeve assembly 50 comprises a tubular cutting sleeve 54 mounted onto the end of tubular shaft 52, the cutting sleeve 54 extending radially outward to have both a larger internal diameter than the internal diameter of bore 53, in order to define a chamber 56 which receives the cutting disk 32 of the punch assembly 30, as well as the plug 104 which is removed from the aortic wall 100, and to have a larger external diameter than the external diameter of tubular shaft 52. The distal end of the cutting sleeve 54 is beveled or sharpened to provide an annular cutting rim 55. The size and configuration of the cutting rim 55 and sleeve 54 are such that when they are advanced against and over the punch disk 32, a shearing or cutting action is effected.

Figure 4:
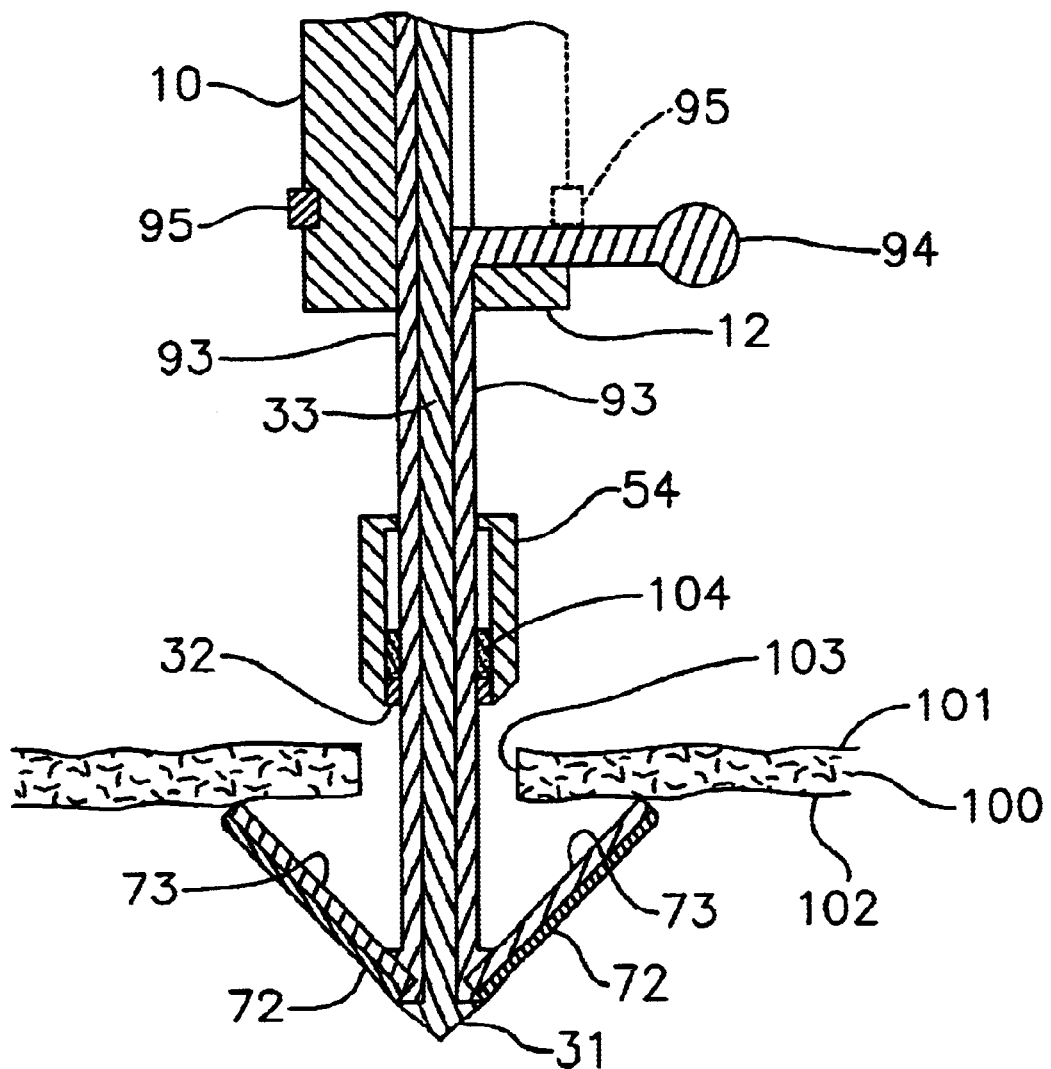
FIG. 4 is a partial cross-sectional view similar to FIG. 3, showing the ram advanced and the dam deployed against the aortic wall.
Figure 5:
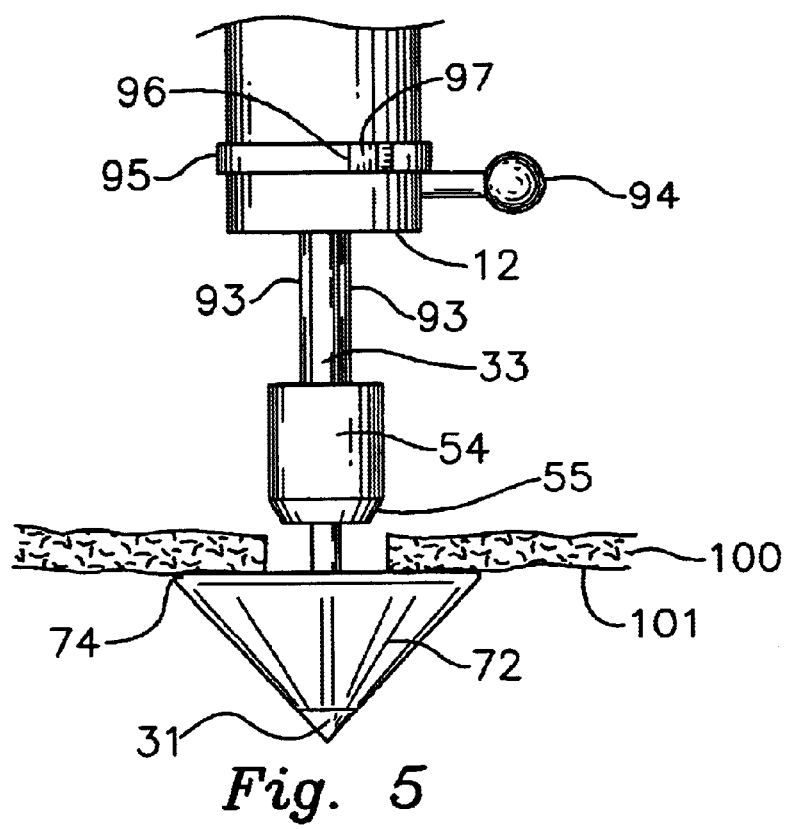
FIG. 5 is a partial view of the device similar to FIG. 4, showing the ram advanced and the dam deployed against the aortic wall.

Affixed immediately to the proximal side of punch head 31 on the punch shaft 33 is the elastic dam assembly 70, the means for occluding blood flow through the opening 103 in the aortic wall 100. Elastic dam assembly 70 comprises a tubular elastic membrane or sheet material 72 impermeable to blood, preferably formed of a polymeric material, which in the passive, non-stretched state has a generally cylindrical or a very tight conical configuration of minimal diameter snugly encircling the shaft 33. The membrane 72 is mounted onto, is formed integrally with, or encases a plurality of relatively rigid, generally linear struts or rib members 73, generally aligned in the axial or longitudinal direction and evenly spaced in the circumferential direction. The distal end 75 of the elastic membrane 72 is securely attached to or affixed around the shaft 33 by fixation means or ring member 71, while the proximal end 76 of the membrane 72 is non-attached to any portion of the punch assembly 30 and defines a sealing rim 74, which may be formed in a beaded or thickened configuration to provide a better seal against the interior side 101 of the aortic wall 100. The membrane 72 is mounted such that it may be flared outwardly in an umbrella-like fashion into a conical active configuration by advancement of the deployment ram assembly 90 toward the fixed distal end 75 and against the ribs 73, with the ribs 73 being pushed away from the shaft 33 at an acute angle to stretch, support and extend the elastic membrane 72, and with the expanded sealing rim 74 thus presenting a relatively large circumference, as shown in FIGS. 4 and 5. When the deployment ram assembly 90 is retracted to remove the pressure against the rib members 73, the elasticity of the membrane 72 causes it to retract into the passive cylindrical configuration of minimal diameter tightly encircling the shaft 33.

Figure 6:
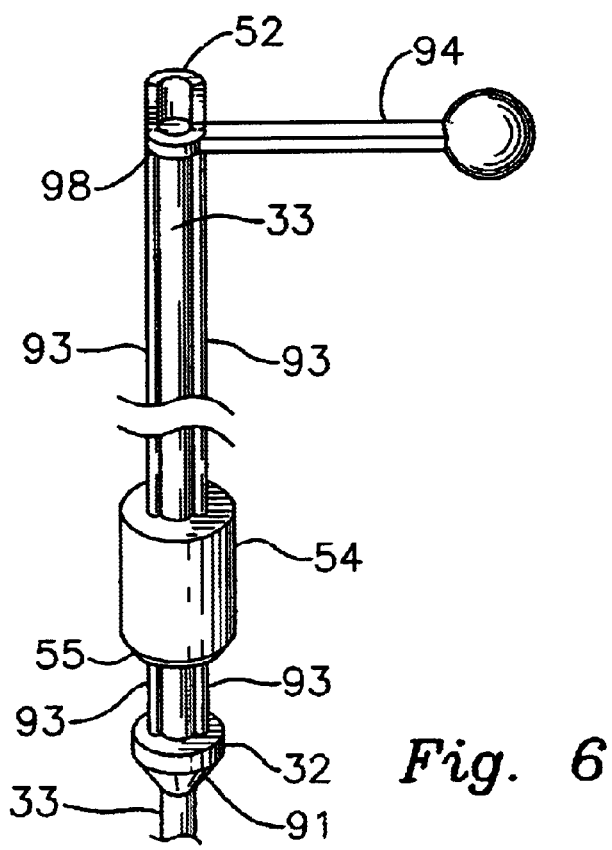
FIG. 6 is a partial, exposed view of the device showing the ram deployment assembly.

The means to deploy or expand the elastic membrane 72, deployment ram assembly 90, is mounted parallel with the punch shaft 33, and comprises a pair of parallel shaft members or rods 93 connected at their proximal end by a semi-circular bridging member 98 to a transversely extending handle 94, which is positioned within ram guide slot 19 of instrument housing 10, such that the ram assembly 90 is movable in the axial direction relative to the housing 10, as shown in FIG. 6. The distal portion of the deployment ram assembly 90 extends out of the instrument housing 10, the parallel shafts 93 extending through the proximal end of the cutting sleeve 54 and through apertures in the cutting disk 32. The parallel shafts 93 connect to a beveled, curved or cone-shaped head or distal end 91. The distal portion of the beveled head 91 fits within the sealing rim 74 of the elastic dam assembly 70 in its passive condition when the deployment ram assembly 90 is advanced toward the fixation ring 71, such that its movement in the distal direction results in it being positioned internally within the tubular elastic membrane 72 in order to effect expansion of the membrane 72 as it is advanced. The outer diameter and angle of the beveled head 91, as well as the distance of travel relative to the dam assembly 70, is such that the membrane 72 is significantly expanded when the ram assembly 90 is fully advanced, with the sealing rim 74 presenting a relatively large circumference to abut the internal side 101 of the aortic wall 100 sufficient distance from the hole 103 to provide room for the surgeon to apply the sutures. Means to lock the deployment ram assembly 90 in the advanced position are provided, and as shown comprises an annular locking collar 95 having of collar slot 96 of sufficient width to allow passage of the ram handle 94 from one side to the other. The locking collar 95 is positioned in an annular collar channel 97 located on the instrument housing 10 such that the collar 96 may be rotated relative to the housing 10. With the collar slot 96 aligned with the ram guide slot 19, as shown in FIGS. 1, 2 and 3, the ram assembly 90 may be advanced to the deployment position, whereupon the locking collar 95 is rotated such that the collar slot 96 is no longer aligned with the ram guide slot 19 and the collar 95 prevents movement of the ram assembly 90 in the proximal direction, as shown in FIGS. 4 and 5.

To create the hole 103 in the aortic wall 100 to perform anastomosis of the vein graft, the surgeon creates a small slit with a scalpel in the aortic wall 100 and introduces the punch head 31 of the device into the slit, or using the punch head 31 alone to penetrate the aortic wall 100, advances the instrument housing 10 such that the punch head 31, the elastic dam assembly 70 and the cutting disk 32 are positioned within the interior of the aortic wall 100, as shown in FIG. 2. The surgeon next advances the cutting sleeve assembly 50 relative to the instrument housing 10 and the punch head assembly 30, thereby causing a circular plug 104 to be removed from the aortic wall 100 because of the interaction between the annular cutting rim 55 and the punch disk 32. The cutting sleeve assembly 50 is then locked in the advanced position, as shown in FIG. 3, by inserting locking pin 16 into the pin receiving aperture 58 of the tubular shaft 52. By locking the cutting assembly 50 in the advanced positioned, the combination of the punch head disk 32 and the cutting sleeve 54 create a sealed chamber 56, such that the aortic plug 104 is retained therein and not released into the blood stream. The deployment ram assembly 90 is then advanced relative to the dam assembly 70 and the punch assembly 30, and is locked in the advanced position by rotating locking collar 95, as shown in FIGS. 4 and 5. This causes expansion of the elastic membrane 72, the beveled head 91 of the ram assembly 90 pressing radially outward against the rib members 73. With the membrane 72 in the open, conical configuration, the instrument housing 10 is slightly withdrawn, such that the sealing rim 74 of the membrane 72 seats firmly against the interior side 101 of the aortic wall 100. In this manner, blood within the aorta is prevented from passing through the hole 103 in the aortic wall 100 while the vein graft is being sutured in place. The vein graft is loosely sutured in known manner with the device in place. Once the initial suturing is completed, the device is advanced slightly, the locking collar 95 is rotated to align the collar slot 96 with the ram guide slot 19 to allow movement of the handle 94 in the proximal direction and the deployment ram assembly 90 is retracted. With the beveled head 91 withdrawn, the elasticity of the membrane 72 causes it to resume its passive cylindrical shape (as in FIG. 3), its outer diameter being smaller than the diameter of the hole 103. In this passive configuration, the entire device is then removed from the hole 103 in the aortic wall 100 and between the sutures, with the surgeon quickly tightening the vein graft sutures to secure the vein against the aortic wall 100.

It is contemplated that equivalents and substitutions to certain elements set forth above may be obvious to those skilled in the art, and the true scope and definition of the invention therefore is to be as set forth in the following claims.

I claim:

1. An anastomosis punch device having means to create an opening in an aortic wall and means to block flow of blood through said opening, the device comprising:
 a generally elongated, unitary, tubular housing having a proximal end and a distal end;
 a punch assembly comprising a shaft extending from said distal end of said housing, a punch head mounted on the distal end of said shaft, and a cutting disk fixedly mounted intermediately on said shaft, said punch assembly being fixed relative to said housing;

a cutting sleeve assembly comprising a tubular shaft, a bore within said tubular shaft, a cutting sleeve mounted onto said tubular shaft and a chamber defined by said cutting sleeve, wherein the diameter of said cutting sleeve is greater than the diameter of said tubular shaft, wherein said cutting sleeve and said chamber are disposed completely external to said housing and adjacent said distal end of said housing prior to initiation of a cutting operation, and wherein said tubular shaft extends through both said distal end and said proximal end of said housing, and where said cutting sleeve is axially movable relative to said housing and said punch assembly;

an elastic dam assembly affixed to said punch assembly, wherein said dam assembly comprises a tubular impermeable elastic membrane and longitudinally extending rigid rib members supporting said elastic membrane, wherein said elastic membrane has a distal end attached to said punch assembly and a non-attached proximal end defining a sealing rim, said elastic membrane having a generally cylindrical passive configuration of minimal diameter and a generally conical active expanded configuration, and wherein said distal end of said elastic membrane is affixed to said punch assembly shaft proximally adjacent to said punch head and said proximal end of said elastic membrane is distally adjacent to said cutting disk when in said passive configuration;

a deployment ram assembly for expanding said elastic membrane from said passive configuration to said active configuration, said deployment ram assembly comprising a parallel shaft external to said punch assembly shaft, a beveled head joined to said parallel shaft, and a handle connected to said parallel shaft and extending radially from said housing, said parallel shaft extending from said distal end of said housing such that said beveled head is disposed distally adjacent said cutting disk and proximally adjacent said proximal end of said elastic membrane prior to advancement of said deployment ram assembly for deployment of said elastic membrane, wherein said deployment ram assembly is axially movable relative to said housing, said bunch assembly and said elastic dam assembly, such that said beveled head advances internally relative to said elastic membrane and pushes outwardly against said rib members when advanced in the distal direction relative to said elastic membrane.

2. The device of claim 1, where said deployment ram assembly comprises a pair of parallel shafts.

3. The device of claim 2, where said deployment parallel shafts are positioned adjacent said punch assembly shaft and extend through said cutting sleeve and said cutting disk.

4. The device of claim 1, where said punch assembly shaft is positioned within said cutting sleeve assembly bore, and where said cutting disk is received within said chamber when said cutting sleeve assembly is moved distally relative to said punch assembly.

5. The device of claim 4, further comprising cutting sleeve locking means to lock said cutting sleeve assembly in position relative to said housing and said punch assembly when said cutting sleeve assembly is moved distally relative to said punch assembly, such that said cutting disk is positioned within said chamber.

6. The device of claim 1, further comprising means to lock said deployment ram assembly in position relative to said punch assembly and said elastic membrane when said deployment ram assembly is moved distally relative to said punch assembly and said elastic membrane.

7. The device of claim 6, wherein said means to lock said deployment ram assembly comprises a rotatable annular collar mounted onto said housing, said collar having a slot sized to allow passage of said handle, wherein said handle can be locked on the distal side of said collar by rotating said collar about said housing.

8. The device of claim 5, wherein said cutting sleeve locking means comprises in combination a transverse bore positioned in said housing, a pin receiving aperture positioned in said cutting sleeve tubular shaft, and a locking pin positioned within said transverse bore which is adapted for insertion into said pin receiving aperture when said pin receiving aperture is aligned with said transverse bore by advancing said cutting sleeve assembly distally relative to said housing.

* * * * *